(12) United States Patent
Studer

(10) Patent No.: US 7,758,645 B2
(45) Date of Patent: Jul. 20, 2010

(54) MODULAR INTERVERTEBRAL IMPLANT OR INTERVERTEBRAL DISK PROSTHESIS

(75) Inventor: Armin Studer, Cham (CH)

(73) Assignee: Synthes USA, LLC, West Chester, PA (US)

(*) Notice: Subject to any disclaimer, the term of this patent is extended or adjusted under 35 U.S.C. 154(b) by 908 days.

(21) Appl. No.: 11/542,491

(22) Filed: Oct. 2, 2006

(65) Prior Publication Data

US 2007/0067037 A1 Mar. 22, 2007

Related U.S. Application Data

(63) Continuation of application No. PCT/CH2004/000209, filed on Apr. 2, 2004.

(51) Int. Cl.
*A61F 2/44* (2006.01)

(52) U.S. Cl. ............... 623/17.13; 623/17.11; 623/17.15

(58) Field of Classification Search .... 623/17.11–17.16
See application file for complete search history.

(56) References Cited

U.S. PATENT DOCUMENTS

| 4,759,769 A | 7/1988 | Hedman et al. ............ 623/17 |
| 5,360,430 A | 11/1994 | Lin |
| 5,370,697 A | 12/1994 | Baumgartner |
| 6,375,682 B1 | 4/2002 | Fleischmann et al. |
| 6,758,862 B2 | 7/2004 | Berry et al. ............... 623/17.16 |
| 2003/0014111 A1 | 1/2003 | Ralph et al. |
| 2003/0187506 A1* | 10/2003 | Ross et al. ............... 623/17.13 |
| 2003/0233146 A1* | 12/2003 | Grinberg et al. ......... 623/17.14 |

OTHER PUBLICATIONS

Notice of the Reason for the Rejection, App. No. 2007-505351, Japanese Patent Office, drafted Feb. 4, 2010 (English translation provided).*

* cited by examiner

*Primary Examiner*—Eduardo C Robert
*Assistant Examiner*—Julianna N Harvey
(74) *Attorney, Agent, or Firm*—Stroock, Stroock & Lavan LLP

(57) ABSTRACT

A modular intervertebral implant or a modular intervertebral disk prosthesis has a middle piece or central section equipped with elements for detachable fixation to one or two apposition plates designed to rest against the base plate or cover plate of an intervertebral body. A modular kit of such modular implants or disks includes n central sections and m apposition plates, where n=2 and m=4 and preferably n=3 and m=6. The surfaces of the apposition plates that face the central section have elements complementary to the elements for detachable fixation on the central section.

12 Claims, 3 Drawing Sheets

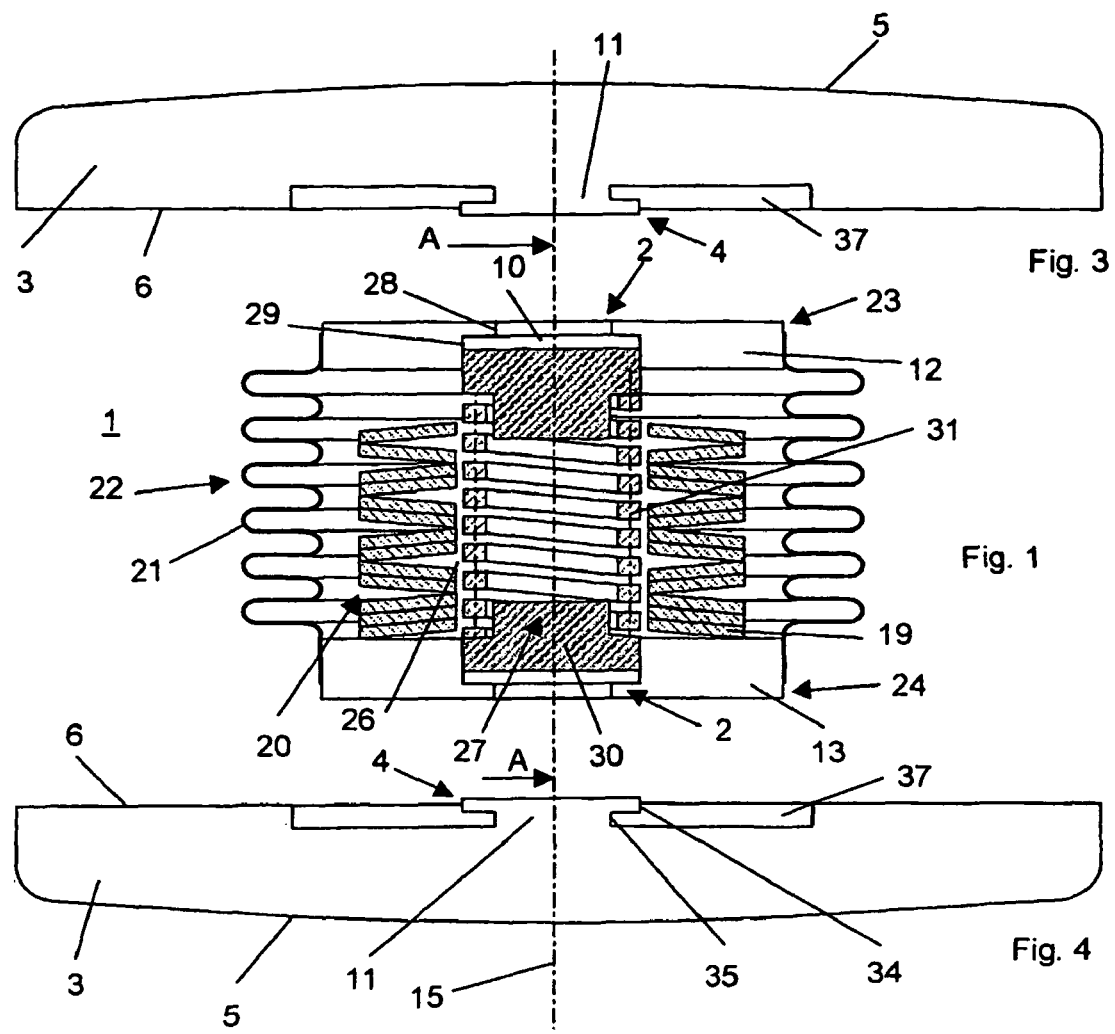
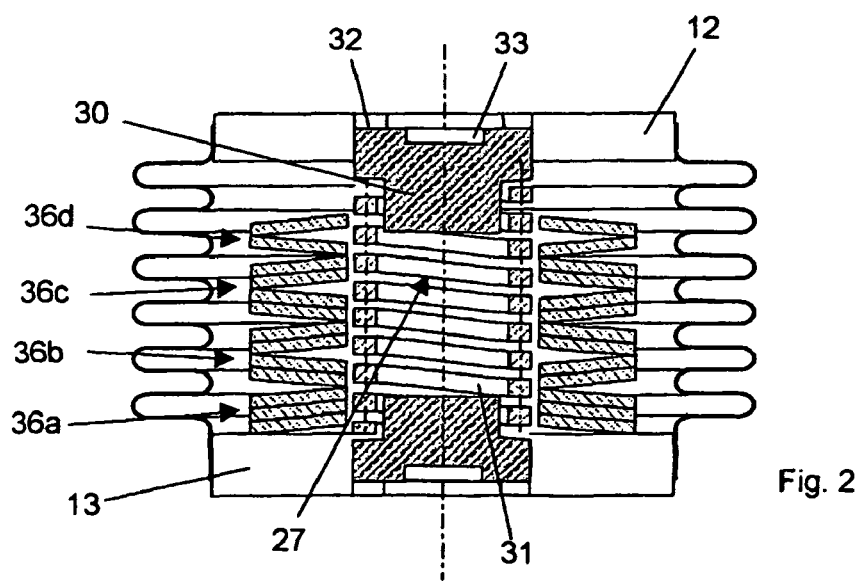

MODULAR INTERVERTEBRAL IMPLANT OR INTERVERTEBRAL DISK PROSTHESIS

CROSS-REFERENCE TO RELATED APPLICATION

This is a continuation of pending International Application No. PCT/CH2004/000209, filed Apr. 2, 2004, the entire contents of which are expressly incorporated herein by reference thereto.

FIELD OF THE INVENTION

The invention relates to a modular intervertebral implant or to a modular intervertebral disk prosthesis with different middle pieces and a number of apposition plates of different construction that can be detachably fastened thereto.

BACKGROUND OF THE INVENTION

As is known, a sufficient number of different implants should be available to the surgeon in order for the surgeon to choose the appropriate implant based on the segment of the spine affected, the weight of the patient, the particular circumstances of the case, and so on.

SUMMARY OF THE INVENTION

The invention is to provide a remedy here. It is an object of the invention to provide a modular intervertebral implant or a modular intervertebral disk prosthesis, which is present in the form of a construction set of a number of middle pieces (for patients of different weight as well as for patients able to move to a different extent) and a number of apposition plates of different constructions, which can be detachably attached thereto, so that the surgeon himself, before the operation, can assemble the implant, which, in his opinion, is optimum and, if necessary, adapt it even during the surgery to the anatomical circumstances and requirements by exchanging suitable middle parts or apposition plates.

Pursuant to the invention, this objective is accomplished with a middle part, which has means for detachable attachment to an apposition plate; an apposition plate, which has means corresponding to the means of the middle part for detachable attachment to the middle part; a modular intervertebral implant or intervertebral disk prosthesis, which has the middle part and two of the apposition plates that are detachably attachable to each other, and a modular construction set, which has a number of different middle parts and different apposition plates.

The advantages achieved by the invention lie essentially therein that it permits a simple equalization in the case of anatomically different vertebrae, such as the combination of the sacrum 1 lumbar vertebra No. 5 (S1/L5).

In a preferred embodiment, the upper end and lower end of the middle piece are each provided with means for the detachable attachment to an apposition plate. By these means, different apposition plates can be mounted at the two ends of the middle piece. This makes possible an individual adaptation of the intervertebral implant, which is assembled from the middle part and the end plates.

Preferably, the means for the detachable attachment of the middle part to the apposition plates can be brought into engagement parallel to the longitudinal axis, so that a simple assembly of the intervertebral implant is attainable.

In a different embodiment, the means can be locked by a rotation of the middle piece, concentric with the longitudinal axis and relative to an apposition plate. Preferably, the means are realized in the form of a female or male part of a bayonet lock. The bayonet lock may be constructed as a rotary lock, so that a simple operation becomes possible.

In yet another embodiment, the middle part can be deformed elastically parallel to its longitudinal axis and has a progressive spring performance curve f. By means of the progressive spring performance curve f, the middle piece can be advantageously used for loads of patients of different weight. For example, the progressivity of the spring performance curve f can be constructed so that:

a first partial range is present for a spring deflection of 0 mm to 0.5 mm with a spring rate of between 450 N/mm and 550 N/mm and preferably of approximately 500 N/mm, so that the middle piece is suitable for patients weighing between 40 and 65 kg, a second partial range is present for the spring deflection between 0.5 mm and 1.0 mm with a spring rate of between 1400 N/mm and 1600 N/mm and preferably of approximately 1500 N/mm, so that the middle piece is suitable for a patient weighing between 60 and 100 kg and a third partial range is present for the spring deflection between 1.0 mm and 1.5 mm with a spring rate of between 2500 N/mm and 3500 N/mm and preferably of approximately 3000 N/mm, said that the middle piece is suitable for loads of a patient weighing between 100 and 140 kg.

Instead of a performance curve with three partial ranges, it is also possible to have only two suitable partial ranges with different spring rates.

In a further embodiment, the middle piece, at each axial end, comprises an end plate, which is disposed transversely to the longitudinal axis and has axially on the outside the female part of the bayonet lock. The male part of the bayonet lock, constructed in complementary fashion, would then have to be mounted at the surfaces of the apposition plates directed against the middle piece.

In a preferred embodiment of the inventive apposition plate, the latter comprises means for the detachable attachment to one of the above-listed embodiments of the middle piece and has an outer surface, which is suitable for apposition to the base or covering plate of a body of a vertebra and an inner surface with the means. Preferably, the outer surface is curved convexly to the outside.

In a different embodiment, the outer surface of the apposition plate and the inner surface include an acute angle $\alpha$, which preferably ranges from 2° to 7°.

In yet another embodiment, the outer surface of the apposition plate has three-dimensional structuring.

The inventive, modular intervertebral implant or modular intervertebral disk prosthesis comprises preferably a middle piece according to one of the embodiments described above and two apposition plates according to one of the embodiments described above.

Furthermore, the invention comprises a modular construction set with n middle pieces in accordance with one of the embodiments described above and m apposition plates in accordance with one of the embodiments described above, the modular construction set comprising $n \geq 2$ middle pieces and $m \geq 4$ apposition plates and preferably $n \geq 3$ middle pieces and $m \geq 6$ apposition plates. The modular construction set makes an optimum adaptation to the intervertebral implant or intervertebral disk prosthesis, which is to be implanted, possible and enables the intervertebral implant to be advantageously assembled in situ.

Preferably, at least two of the m apposition plates have a different height.

BRIEF DESCRIPTION OF THE DRAWINGS

The invention and further developments of the invention are explained in even greater detail in the following by means of the partially diagrammatic representations of several examples. In the drawings:

FIG. 1 shows a section through an embodiment of the inventive middle part;

FIG. 2 shows a section along line A-A in FIG. 1;

FIG. 3 shows an embodiment of an apposition plate, which can be fastened above the middle part;

FIG. 4 shows the apposition plate of FIG. 3 fastened below the middle part;

DETAILED DESCRIPTION OF THE INVENTION

Figure 5:
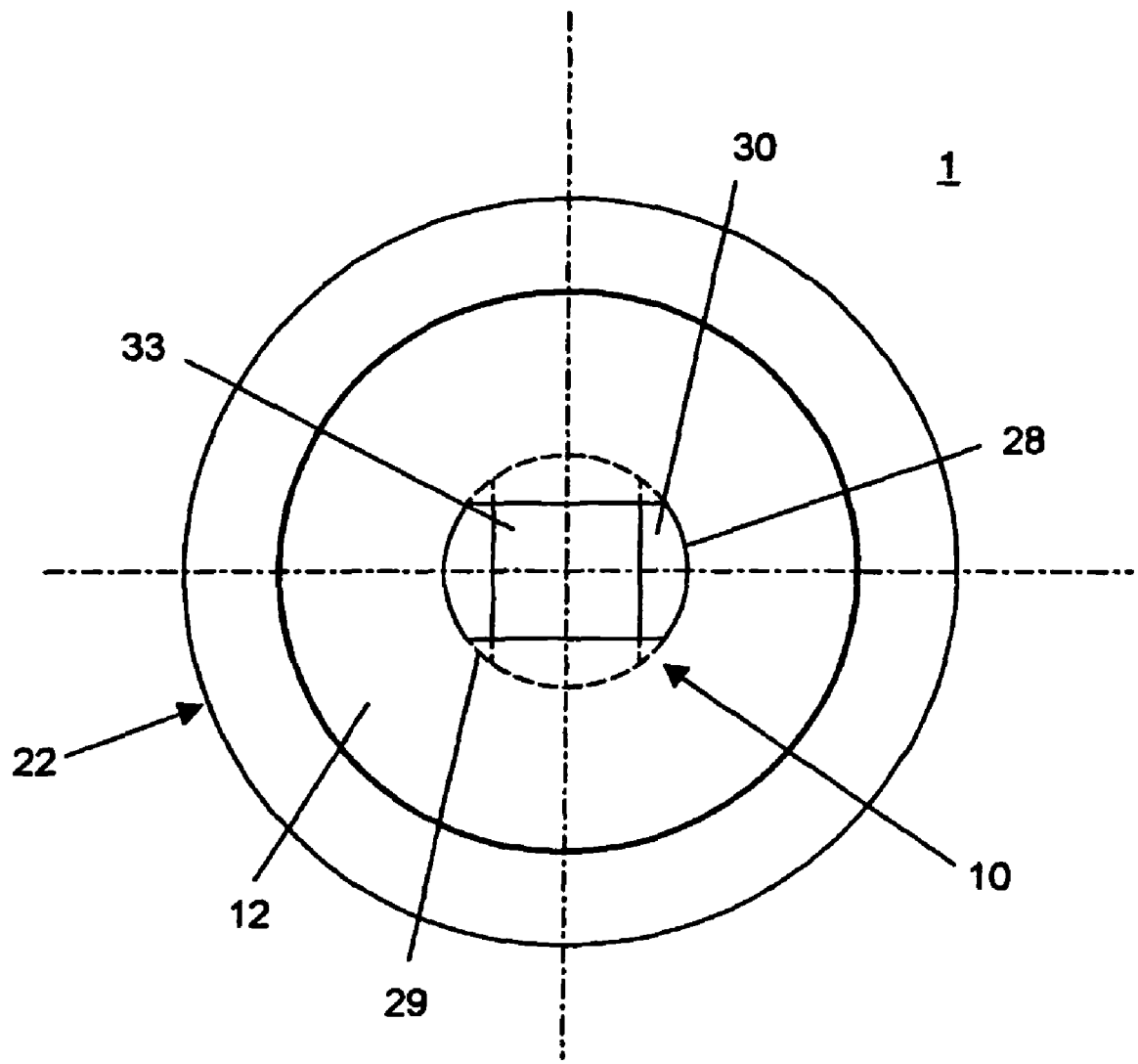
FIG. 5 shows a plan view of the middle part represented in FIGS. 1 and 2.

FIGS. 1, 2, and 5 show an embodiment of a middle part 1, which has a first end 23, a second end 24, a hollow cylindrical elastic means 20, which is disposed coaxially with a longitudinal axis 15, a coaxial outer casing 22, which is constructed as corrugated bellows 21, end plates 12,13, each of which is disposed axially at an end transversely to longitudinal axis 15, and axially elastic blocking means 27, which is disposed in cavity 26 of elastic means 20 for blocking a bayonet lock disposed in end plates 12,13.

End plates 12,13 comprise terminally a female part 10 of the bayonet lock in the form of an outside oval opening 28 (FIG. 5) and an axially adjoining cylindrical undercut 29, so that the complementary male parts 11 of the bayonet locks, which are disposed at apposition plates 3 (FIGS. 3 and 4), can be introduced and, by rotation about longitudinal axis 15, fixed axially. Blocking means 27, which comprise two plugs 30 here, which are disposed axially one above the other, and a spring 31, which is disposed coaxially between the plugs 30, serve to block the male parts 11 of the bayonet locks. The plugs 30 are pressed by spring 31 against end plates 12,13. At each of their axially outer ends 32, the plugs 30 have a groove 33 (FIG. 5), which is disposed transversely to longitudinal axis 15 for accommodating the front segments 34 of male parts 11 (FIGS. 3 and 4) of the bayonet locks.

The male parts 11 of the bayonet locks are shown in FIGS. 3 and 4. They each comprise a front segment 34, which is constructed to be complementary to the oval opening 28 in the female parts 10 of the bayonet locks. Each male part 11 also comprises a rear segment 35, which is constructed cylindrically and does not protrude radially over the front segment 34, so that the male parts 11, when introduced into the female parts 10, can be rotated about longitudinal axis 15 until the front segments 33 snap into grooves 33 at plugs 30. During the introduction, the plugs 30, moreover, are shifted axially against one another, so that, after rotation of the male parts 11, when the front segments 34 are aligned with the grooves 33, the plugs 30 are shifted by the force of spring 31 against the end plates and the front segments 34 of the male parts 11 are blocked in grooves 33.

The middle part 1 furthermore comprises elastic means 20, which are disposed coaxially with longitudinal axis 15 and, on the outside, around elastic means 20, an outer casing 22, which is constructed as corrugated bellows 21. The latter may be welded to, caulked to, or pressed into the two end plates 12,13. In the embodiment shown here, elastic means 20 is composed of disk spring packages 36a; 36b; 36c; 36d (FIG. 2) with identical disk springs 19. However, the first disk spring package 36a includes a disk spring group comprising three equidirectional multi-leaf disk springs 19, the second and third disk spring packages 36b,36c each include two oppositely directed groups of two equally directional multi-leaf disk springs 19 each. The fourth disk spring package 36d includes two oppositely directed disk springs 19. A progressive spring performance curve of the elastic means 20 may be attained by this configuration of the disk spring packages 36a,36b,36c,36d.

FIGS. 3 and 4 show an upper apposition plate 3, which is disposed at upper end 23 of middle part 1 transversely to longitudinal axis 15 and is suitable for lying in contact with the base plate of a body of a vertebra, and a lower apposition plate 3, which is disposed at lower end 24 of middle part 1 transversely to longitudinal axis 15 and is suitable for lying in contact with the covering plate of a body of a vertebra. The two apposition plates 3 have a surface 5, which is curved convexly towards the outside and, at their inner surfaces 6, a depression 37, which is concentric with longitudinal axis 15, with the integrated male part 11 of the bayonet lock.

Figure 6:
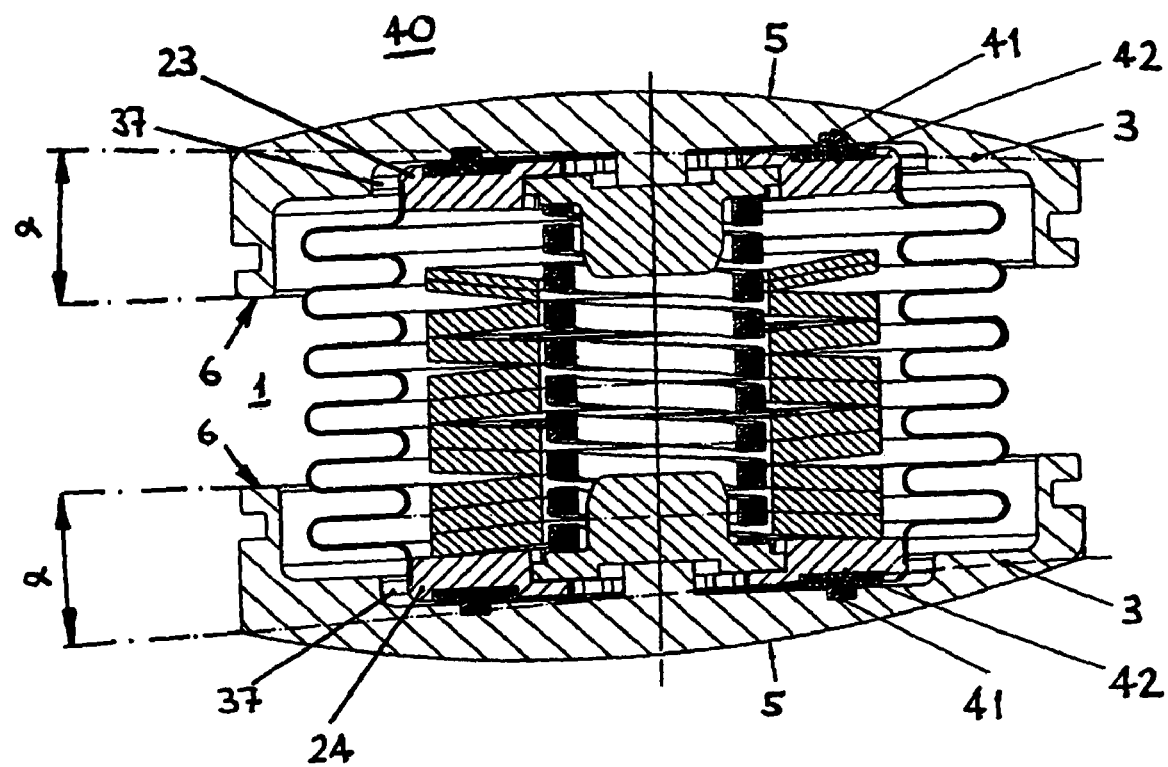
FIG. 6 shows an antero-posterior section through an embodiment of the inventive, modular intervertebral disk prosthesis.

FIG. 6 shows an embodiment of a modular intervertebral implant 40 with a middle part 1, an upper apposition plate 3 at the upper end 23 of the middle part 1, and a lower apposition plate 3 at the lower end 24 of the middle part of 1. The middle part 1 and the apposition plates 3 differ from the embodiments shown in FIGS. 1-5 only in that a ring 41,42 of a ceramic material, concentric with longitudinal axis 15, is disposed in each of the depressions 37 at the inner surfaces 6 of the apposition plates 3 and, complementarily, on the outside at end plates 12,13 of the middle part 1, and that the outer surfaces 5 of the apposition plates 3 enclose an angle $\alpha$ of 3° with inner surfaces 6. This slope of apposition plates 3 is constructed so that the total height of the intervertebral implant 40 is less dorsally than ventrally. The ceramic rings 41,42 assume a sealing function, so that body fluid cannot penetrate into the interior of the intervertebral implant.

I claim:

1. An intervertebral disk prosthesis or intervertebral implant having a central longitudinal axis, the disk comprising:

an upper apposition plate arranged transversely to the longitudinal axis, the upper apposition plate including an upper surface for contacting a lower plate of a first vertebra and a lower surface opposite the upper surface, the lower surface having a male part;

a lower apposition plate arranged transversely to the longitudinal axis, the lower apposition plate including a lower surface for contacting an upper plate of a second vertebra and an upper surface opposite the lower surface, the upper surface having a male part;

a middle piece including:

a first plate arranged transversely to the longitudinal axis, the first plate including an upper surface, a lower surface and a female part formed in the upper surface for engaging the male part of the upper apposition plate;

a second plate arranged transversely to the longitudinal axis, the second plate including a lower surface, an upper surface and a female part formed in the lower surface for engaging the male part of the lower apposition plate;

a first blocking means operatively associated with the first plate, the first blocking means including a lower surface;

a second blocking means operatively associated with the second plate, the second blocking means including an upper surface;

a spring arranged co-axially with the longitudinal axis, the spring operatively coupled to the lower surface of the first blocking means and the upper surface of the second blocking means;

an elastic means arranged co-axially with the longitudinal axis and operatively coupled to the upper surface of the second plate and spaced by a distance from the lower surface of the first plate in a no-load state, the elastic means coming into contact with the lower surface of the first plate when the spring is compressed; and an outer casing circumferentially disposed about the spring and the elastic means, the outer casing operatively associated with the first and second plates.

2. The intervertebral disk prosthesis of claim 1, wherein the middle piece is lockable relative to the upper and lower apposition plates by rotating the middle piece concentric with the longitudinal axis and causing the male parts of the upper and lower apposition plates to engage the female parts of the first and second plates.

3. The intervertebral disk prosthesis of claim 1, wherein the elastic means has a progressive spring performance curve.

4. The intervertebral disk prosthesis of claim 3, wherein the spring performance curve has a spring rate of between 450 N/mm and 550 N/mm in a first partial region and a spring rate of between 1400 N/mm and 1600 N/mm in a second partial region.

5. The intervertebral disk prosthesis of claim 3, wherein the spring performance curve has a spring rate between 2500 N/mm and 3500 N/mm in a first partial region.

6. The intervertebral disk prosthesis of claim 1, wherein the upper surface of the upper apposition plate and the lower surface of the lower apposition plate are curved convexly.

7. The intervertebral disk prosthesis of claim 1, wherein the male parts of the upper and lower apposition plates are the male part of a bayonet lock and the female parts of the first and second plates are the female parts of a bayonet lock.

8. The intervertebral disk prosthesis of claim 1, wherein the female part of the first plate includes an oval shape opening towards the upper surface of the first plate and a cylindrical shaped undercut directly below the oval shaped opening and the female part of the second plate includes an oval shape opening towards the lower surface of the second plate and a cylindrical shaped undercut directly above the oval shape opening.

9. The intervertebral disk prosthesis of claim 1, wherein the elastic means is composed of disk spring packages.

10. The intervertebral disk prosthesis of claim 1, wherein the outer casing is a corrugated bellow.

11. The intervertebral disk prosthesis of claim 1, wherein the outer casing is welded to the first and second plates.

12. The intervertebral disk prosthesis of claim 1, wherein the lower surface of the upper apposition plate includes a depression around the male part and the upper surface of the lower apposition plate includes a depression around the male part, and wherein a first ring is disposed in the depression of the upper apposition plate and a second ring is disposed in the depression of the second apposition plate.

* * * * *